US012059261B2

(12) United States Patent
Chen et al.

(10) Patent No.: US 12,059,261 B2
(45) Date of Patent: Aug. 13, 2024

(54) APPARATUS AND METHOD FOR ELECTROCARDIOGRAM (ECG) SIGNAL ANALYSIS AND HEART BLOCK DETECTION

(71) Applicant: Draegerwerk AG & Co. KGaA, Lübeck (DE)

(72) Inventors: Yu Chen, Andover, MA (US); Kristen M. Bean, Newburyport, MA (US)

(73) Assignee: Drägerwerk AG & Co. KGaA (DE)

( * ) Notice: Subject to any disclaimer, the term of this patent is extended or adjusted under 35 U.S.C. 154(b) by 185 days.

(21) Appl. No.: 17/527,768

(22) Filed: Nov. 16, 2021

(65) Prior Publication Data
US 2022/0202344 A1 Jun. 30, 2022

Related U.S. Application Data
(60) Provisional application No. 63/131,557, filed on Dec. 29, 2020.

(51) Int. Cl.
A61B 5/364 (2021.01)
A61B 5/00 (2006.01)
A61B 5/352 (2021.01)
A61B 5/353 (2021.01)
A61B 5/36 (2021.01)

(52) U.S. Cl.
CPC .............. A61B 5/364 (2021.01); A61B 5/352 (2021.01); A61B 5/353 (2021.01); A61B 5/36 (2021.01); A61B 5/7207 (2013.01)

(58) Field of Classification Search
None
See application file for complete search history.

(56) References Cited

U.S. PATENT DOCUMENTS

| | | | | |
|---|---|---|---|---|
| 11,717,687 B2* | 8/2023 | Sullivan | ................. | A61N 1/365 607/5 |
| 2009/0171227 A1* | 7/2009 | Dziubinski | .......... | A61B 5/7264 600/516 |
| 2011/0208079 A1* | 8/2011 | Babaeizadeh | ............ | A61B 5/35 600/518 |
| 2023/0062753 A1* | 3/2023 | Zhang | ................. | A61B 5/7267 |

* cited by examiner

Primary Examiner — Kennedy Schaetzle
(74) Attorney, Agent, or Firm — Design IP

(57) ABSTRACT

Systems and methods for identifying one or more P-waves in real-time are disclosed. Exemplary implementations may: receive a plurality of signals from an ECG lead configured to be connected with a patient; determine a noise level of the plurality of signals during a pre-determined time interval; identify a plurality of QRS-complex candidates from the received plurality of signals; extract one or more features from each QRS-complex candidate based on the determined noise level of the plurality of signals; cluster, based on the extracted one or more features from each QRS-complex candidate, the plurality of QRS-complex candidates; and identify one or more P-waves from the clustered plurality of QRS-complex candidates. Based on the identified one or more P-waves, a heart block event can be detected.

26 Claims, 7 Drawing Sheets

APPARATUS AND METHOD FOR ELECTROCARDIOGRAM (ECG) SIGNAL ANALYSIS AND HEART BLOCK DETECTION

TECHNICAL FIELD

The present disclosure relates generally to the field of electrocardiogram (ECG) signal analysis. More particularly, the present disclosure relates to the analysis of an ECG waveform including QRS-complexes and P-waves, and the detection of heart block events.

BACKGROUND

Heart block, also called as atrioventricular (AV) block, is an abnormal heart rhythm where the heart beats too slowly (e.g., bradycardia), resulting in the electrical signals being partially or totally blocked between the upper chambers (atria) and lower chambers (ventricles). In other words, heart block is a delay or interruption in the transmission of an impulse from the atria to the ventricles due to an anatomical or functional impairment or disturbance in the cardiac conduction system. The disturbance can be transient or permanent, where the cardiac conductions are delayed, intermittent, or absent.

When a patient is connected to a physiological monitoring device that monitors his or her vital signs (e.g., ECG signals), it is imperative for the device to detect ventricular heart beats accurately and generate heart-rate related alarms (e.g., brady, pause, and asystole) when heart block events occur.

When a patient has a normal atrial morphology and electrical activity, P-waves in the ECG waveform are less than 120 milliseconds (ms) in duration and are small in amplitude, distinct from QRS complexes. Accordingly, ventricular heart beats of the patient can be measured accurately by detecting and analyzing QRS complexes. When a patient has an atrial abnormality (e.g., left atrial enlargement, right atrial enlargement), P-wave morphology can be substantially changed. For example, when a heart block event occurs together with atrial abnormality, the time is increased for atrial depolarization and conduction through the AV node and the His-Purkinje system that constitutes the P-R segments, and therefore, both the amplitude of P-waves and the length of the P-R intervals are increased. The P-waves with large amplitude are often mistakenly identified as ventricular R-waves in the QRS complex, especially when ECG signals are noisy. Additionally, the abnormally increased P-R intervals or the absence of R-waves caused by the heart block will cause P-waves to be mistakenly identified as valid R-waves. Since the identified R-waves are also used to calculate heart rate, the mistakenly identified P-waves may cause the calculated heart rate to be incorrect. As a result, anticipated heart rate related alarms (e.g., brady, pause and asystole) are frequently missed by the physiological monitoring device.

BRIEF DESCRIPTION

There exists a need for improved detection and analysis of ECG waveforms including QRS complexes and P-waves, in order for the physiological monitoring device to accurately identify P-waves when a heart block event occurs and generate heart-rate related alarms in a timely manner. There also exists a need for analyzing ECG waveforms including QRS complexes and P-waves, in order to identify different types of heart block events based on the analysis, thereby assisting clinical providers to promptly identify the medical conditions of the patient and provide treatment as needed.

To resolve at least one or more of the above problems and potentially other present or future problems, one aspect of the present disclosure relates to a system configured for identifying one or more P-waves in real time. The system may include one or more processors configured by machine-readable instructions. The processor(s) may be configured to receive a plurality of signals from an ECG lead configured to be connected with a patient, determine a noise level of the plurality of signals during a pre-determined time interval, and identify a plurality of QRS-complex candidates from the received plurality of signals. The processor(s) may further be configured to extract one or more features from each QRS-complex candidate based on the determined noise level of the plurality of signals, cluster, based on the extracted one or more features from each QRS-complex candidate, the plurality of QRS-complex candidates, and identify one or more P-waves from the clustered plurality of QRS-complex candidates.

Another aspect of the present disclosure relates to a system configured for detecting a heart block event. The system may include a non-transient computer-readable storage medium having executable instructions embodied thereon. The system may include one or more processors configured to execute the instructions. The processor(s) may execute the instructions to receive a plurality of signals from an ECG lead configured to be connected with a patient, determine a noise level of the plurality of signals during a pre-determined time interval, and identify a plurality of QRS-complex candidates from the received plurality of signals. The processor(s) may further execute the instructions to extract one or more features from each QRS-complex candidate based on the determined noise level of the plurality of signals, cluster, based on the extracted one or more features from each QRS-complex candidate, the plurality of QRS-complex candidates, identify one or more P-waves from the clustered plurality of QRS-complex candidates, and detect the heart block event based on the identified one or more P-waves.

Yet another aspect of the present disclosure relates to a method for identifying one or more P-waves in real time. The method may include receiving a plurality of signals from an ECG lead configured to be connected with a patient, determining a noise level of the plurality of signals during a pre-determined time interval, identifying a plurality of QRS-complex candidates from the received plurality of signals. The method may further include extracting one or more features from each QRS-complex candidate based on the determined noise level of the plurality of signals, clustering, based on the extracted one or more features from each QRS-complex candidate, the plurality of QRS-complex candidates, and identifying one or more P-waves from the clustered plurality of QRS-complex candidates.

Yet another aspect of the present disclosure relates to a system configured for detecting a P-wave asystole event. The system may include a non-transient computer-readable storage medium having executable instructions embodied thereon. The system may include one or more processors configured to execute the instructions. The processor(s) may execute the instructions to receive a plurality of signals from an ECG lead configured to be connected with a patient, determine a noise level of the plurality of signals during a pre-determined time interval, and identify a plurality of QRS-complex candidates from the received plurality of signals. The processor(s) may further execute the instructions to extract one or more features from each QRS-complex candidate based on the determined noise level of the plurality of signals, identify one or more P-waves based on the extracted one or more features from each QRS-complex candidate, and detect the P-wave asystole event based on the identified one or more P-waves.

One or more embodiments of the present disclosure provide but not limited to the following advantages. When heart block events occur, P-waves with large amplitude can be accurately recognized even when the ECG signals are noisy and/or there are one or more missed beats in the recorded ECG waveforms. The enlarged P-waves can be differentiated from R-waves even when the P-R interval is increased, and when R-waves do not correspond with P-waves or absent from the ECG waveform. Because of the identification of P-waves, heart-rate related alarms (e.g., brady, pause and asystole) can be generated in an accurate and timely manner. Additionally, one or more embodiments of the present disclosure provides the analysis of ECG waveforms and identification of different types of heart block events. Based on the identification, clinical providers can promptly identify the medical conditions of the patient and provide treatment as needed, thereby improving the clinical workflow.

BRIEF DESCRIPTION OF THE DRAWINGS

In the drawings, like reference numbers generally indicate identical, functionally similar, and/or structurally similar elements.

DETAILED DESCRIPTION

Figure 1:
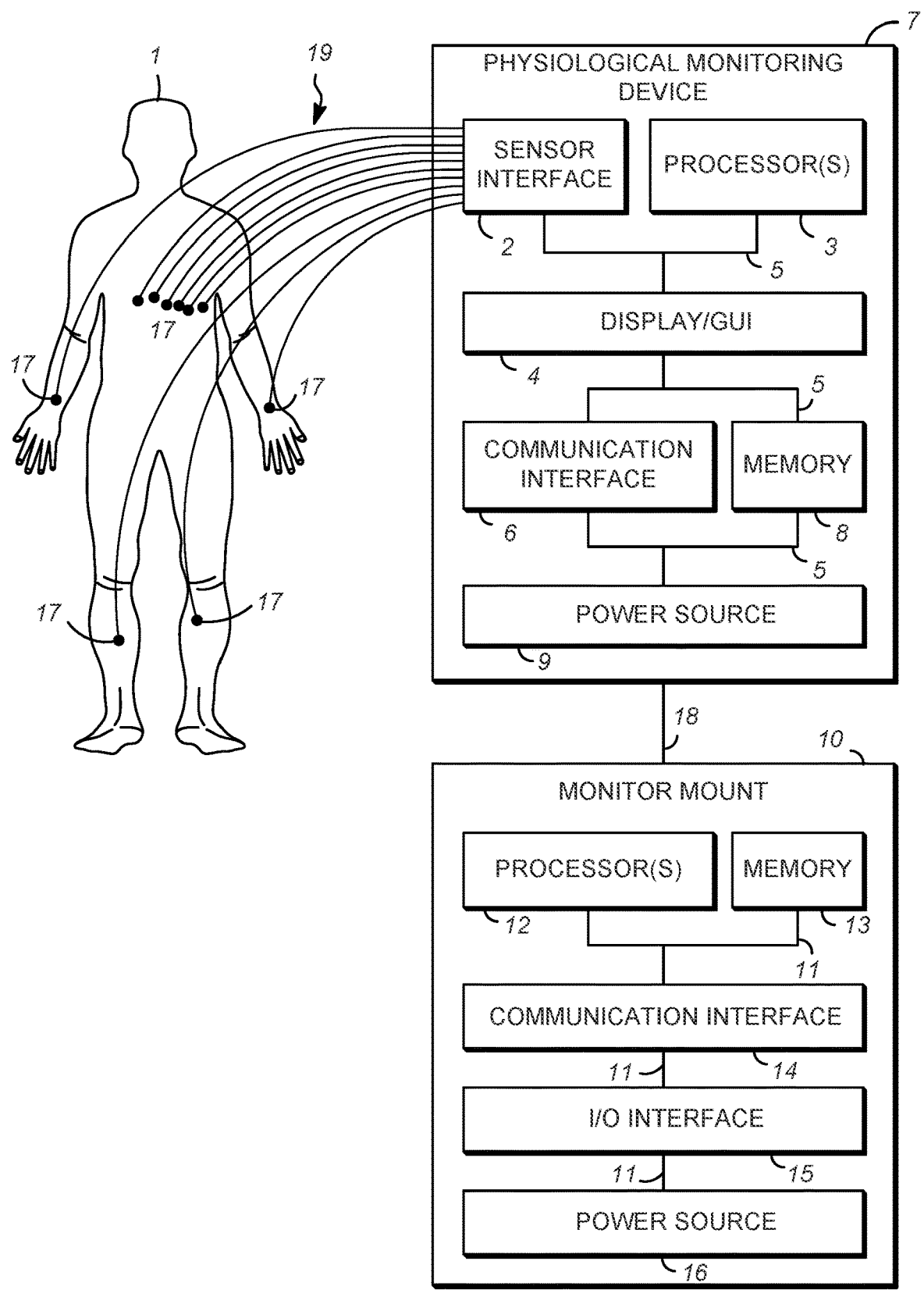
FIG. 1 is a schematic diagram of an exemplary physiological monitoring system with a plurality of surface ECG leads connected to a patient, for analyzing ECG waveforms according to one embodiment of the present disclosure.

In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Directional terminology, such as "top", "bottom", "below", "above", "front", "behind", "back", "leading", "trailing", etc., may be used with reference to the orientation of the figures being described. Because parts of embodiments can be positioned in a number of different orientations, the directional terminology is used for purposes of illustration. It is to be understood that other embodiments may be utilized, and structural or logical changes may be made without departing from the scope defined by the claims. The following detailed description, therefore, is not to be taken in a limiting sense. Directional terminology used in the claims may aid in defining one element's spatial or positional relation to another element or feature, without being limited to a specific orientation.

Instructions may be executed by one or more processors, such as one or more central processing units (CPU), digital signal processors (DSPs), general purpose microprocessors, application specific integrated circuits (ASICs), field programmable logic arrays (FPGAs), or other equivalent integrated or discrete logic circuitry. Accordingly, the term "processor," as used herein refers to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. A "controller," including one or more processors, may use electrical signals and digital algorithms to perform its receptive, analytic, and control functions, which may further include corrective functions. Thus, a controller is a specific type of processing circuitry, comprising one or more processors and memory, that implements control functions by way of generating control signals.

FIG. 1 is a schematic diagram of an exemplary physiological monitoring system with a plurality of surface ECG leads connected to a patient, for detecting and analyzing ECG waveforms according to one embodiment of the present disclosure. As illustrated, the system includes a physiological monitoring device 7 capable of receiving physiological data from various sensors 17 connected to a patient 1, and a monitor mount 10 to which the physiological monitoring device 7 is removably mounted or docked.

As shown in FIG. 1, the physiological monitoring device 7 is, for example, a patient monitor implemented to monitor various physiological parameters of the patient 1 via the sensors 17. The physiological monitoring device 7 includes a sensor interface 2, one or more processors 3, a display/GUI 4, a communications interface 6, a memory 8, and a power source 9. The sensor interface 2 can be implemented in software or hardware and used to connect via wired and/or wireless connections to one or more physiological sensors and/or medical devices 17 for gathering physiological data from the patient 1. The data signals from the sensors 17 include, for example, data related to an electrocardiogram (ECG), non-invasive peripheral oxygen saturation ($SpO_2$), non-invasive blood pressure (NIBP), temperature, and/or tidal carbon dioxide ($etCO_2$), apnea detection, and other similar physiological data.

The communications interface 6 allows the physiological monitoring device 7 to directly or indirectly (via, for example, the monitor mount 10) to communicate with one or more computing networks and devices. The communications interface 6 can include various network cards, interfaces or circuitry to enable wired and wireless communications with such computing networks and devices. The communications interface 6 can also be used to implement, for example, a Bluetooth connection, a cellular network connection, and/or a WiFi connection. Other wireless communication connections implemented using the communications interface 6 include wireless connections that operate in accordance with, but are not limited to, IEEE802.11 protocol, a Radio Frequency for Consumer Electronics (RF4CE) protocol, ZigBee protocol, and/or IEEE802.15.4 protocol.

Additionally, the communications interface 6 can enable direct (i.e., device-to-device) communications (e.g., messaging, signal exchange, etc.) such as from the monitor mount 10 to the physiological monitoring device 7 using, for example, a USB connection. The communications interface 6 can also enable direct device-to-device connection to other devices such as to a tablet, PC, or similar electronic device; or to an external storage device or memory.

The power source 9 can include a self-contained power source such as a battery pack and/or include an interface to be powered through an electrical outlet (either directly or by way of the monitor mount 10). The power source 9 can also be a rechargeable battery that can be detached allowing for replacement. In the case of a rechargeable battery, a small built-in back-up battery (or super capacitor) can be provided for continuous power to be provided to the physiological monitoring device 7 during battery replacement. Communication between the components of the physiological monitoring device 7 (e.g., 2, 3, 4, 6, 8, and 9) are established using an internal bus 5.

As shown in FIG. 1, the physiological monitoring device 7 is connected to the monitor mount 10 via a connection 18 that establishes a communication connection between, for example, the respective communications interfaces 6, 14 of the devices 7, 10. The connection 18 enables the monitor mount 10 to detachably secure the physiological monitoring device 7 to the monitor mount 10. In this regard, "detachably secure" means that the monitor mount 10 can secure the physiological monitoring device 7, but the physiological monitoring device 7 can be removed or undocked from the monitor mount 10 by a user when desired. The connection 18 may include, but is not limited to, a universal serial bus (USB) connection, parallel connection, a serial connection, coaxial connection, a High-Definition Multimedia Interface (HDMI) connection, or other similar connection known in the art connecting to electronic devices.

The monitor mount 10 includes one or more processors 12, a memory 13, a communications interface 14, an I/O interface 15, and a power source 16. The one or more processors 12 are used for controlling the general operations of the monitor mount 10. The memory 13 can be used to store any type of instructions associated with algorithms, processes, or operations for controlling the general functions and operations of the monitor mount 10.

The communications interface 14 allows the monitor mount 10 to communicate with one or more computing networks and devices (e.g., the physiological monitoring device 7). The communications interface 14 can include various network cards, interfaces or circuitry to enable wired and wireless communications with such computing networks and devices. The communications interface 14 can also be used to implement, for example, a Bluetooth connection, a cellular network connection, and a WiFi connection. Other wireless communication connections implemented using the communications interface 14 include wireless connections that operate in accordance with, but are not limited to, IEEE 802.11 protocol, a Radio Frequency For Consumer Electronics (RF4CE) protocol, ZigBee protocol, and/or IEEE 802.15.4 protocol.

The communications interface 14 can also enable direct (i.e., device-to-device) communications (e.g., messaging, signal exchange, etc.) such as from the monitor mount 10 to the physiological monitoring device 7 using, for example, a USB connection, coaxial connection, or other similar electrical connection. The communications interface 14 can enable direct (i.e., device-to-device) to other device such as to a tablet, PC, or similar electronic device; or to an external storage device or memory.

The I/O interface 15 can be an interface for enabling the transfer of information between monitor mount 10, one or more physiological monitoring devices 7, and external devices such as peripherals connected to the monitor mount 10 that need special communication links for interfacing with the one or more processors 12. The I/O interface 15 can be implemented to accommodate various connections to the monitor mount 10 that include, but is not limited to, a universal serial bus (USB) connection, parallel connection, a serial connection, coaxial connection, a High-Definition Multimedia Interface (HDMI) connection, or other known connection in the art connecting to external devices.

The power source 16 can include a self-contained power source such as a battery pack and/or include an interface to be powered through an electrical outlet (either directly or by way of the physiological monitoring device 7). The power source 16 can also be a rechargeable battery that can be detached allowing for replacement. Communication between the components of the monitor mount 10 (e.g., 12, 13, 14, 15 and 16) are established using an internal bus 11.

Figure 2A:
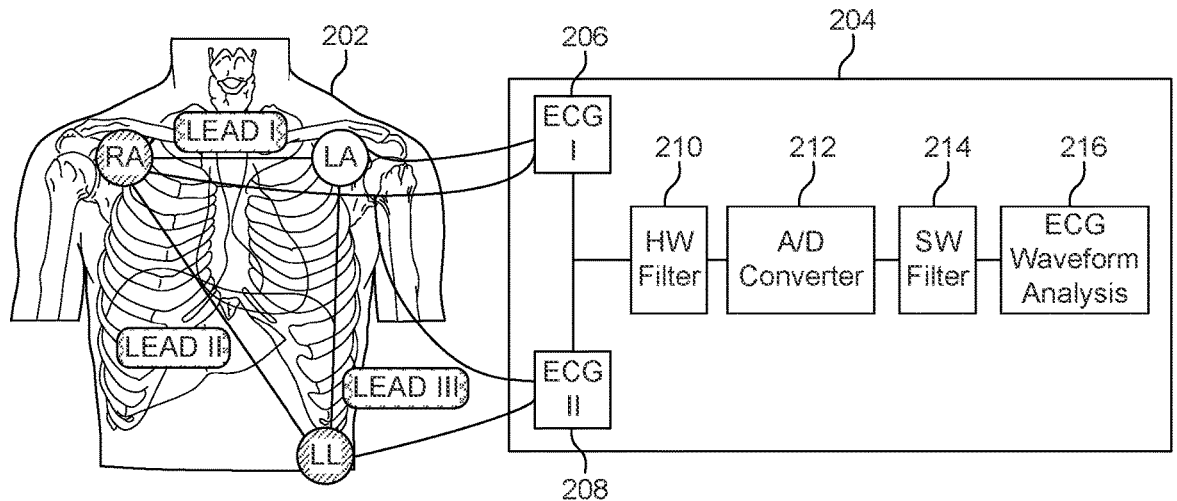
FIG. 2A is a schematic diagram of an exemplary physiological monitoring system with a plurality of surface ECG leads connected to a patient, for analyzing ECG waveforms according to one embodiment of the present disclosure.

FIG. 2A is a schematic diagram of an exemplary physiological monitoring system with a plurality of surface ECG leads connected to a patient for detecting and analyzing ECG waveforms according to one embodiment of the present disclosure. A patient 202 is connected to a plurality of ECG electrodes attached to predetermined positions on the surface of the body (e.g., Left Arm=LA, Right Arm=RA, Left Leg=LL as illustrated in FIG. 2A). As illustrated, two electrodes attached to the patient's left arm (LA) and right arm (RA), respectively, are connected to a physiological monitoring device 204 via the sensor interface 206 and are configured to measure electrical potential signal of the heart from a first vector (e.g., ECG I 206 as illustrated in FIG. 2A). Similarly, two electrodes attached to right arm (RA) and left leg (LL), respectively, are connected to the physiological monitoring device 204 via the sensor interface 208 for ECG signal measurement from a second vector (e.g., ECG II 208 as illustrated in FIG. 2A). The signals from two ECG leads are filtered using hardware filters 210 (e.g., high-pass filters and/or low-pass filters), converted to digital forms using A/D converter 212, and further filtered using software filtering strategies 214 (e.g., low-pass filters). The sampling rate for the conversion may be 100-500 samples per second (sps), for example, 200-500 sps or 150-350 sps. Subsequently, the digital data stream is passed for ECG waveform analysis 216, which will be described in more detail as follows.

It should be noted that the aforementioned embodiments are not limited to the numbers and types of ECG leads used for collecting ECG signals and subsequent ECG waveform analysis, during which P-waves and heart block events can be identified. In other words, the ECG signals used for the subsequent waveform analysis may be received from a single ECG lead, two ECG leads, or more. Additionally, the two or more leads are not limited to ECG I (from electrodes attached to the patient's left arm and right arm) and ECG II (electrodes attached to the patient's right arm and left leg) as illustrated in FIG. 2A. Commonly used ECG configurations include 3-lead, 5-lead, 6-lead, 12-lead. In this way, the overall magnitude and direction of the heart's electrical activity is captured throughout the heartbeat. Depending on the need of the patient (e.g., medical condition of the patient, location of the patient, ECG monitoring device the patient is connected to, and/or medical procedure the patient is applied to), different lead configurations may be used. Accordingly, the disclosed embodiments can be adapted to receive and analyze ECG signals from different leads, and identify P-waves and heart block events as described below.

Figure 2B:
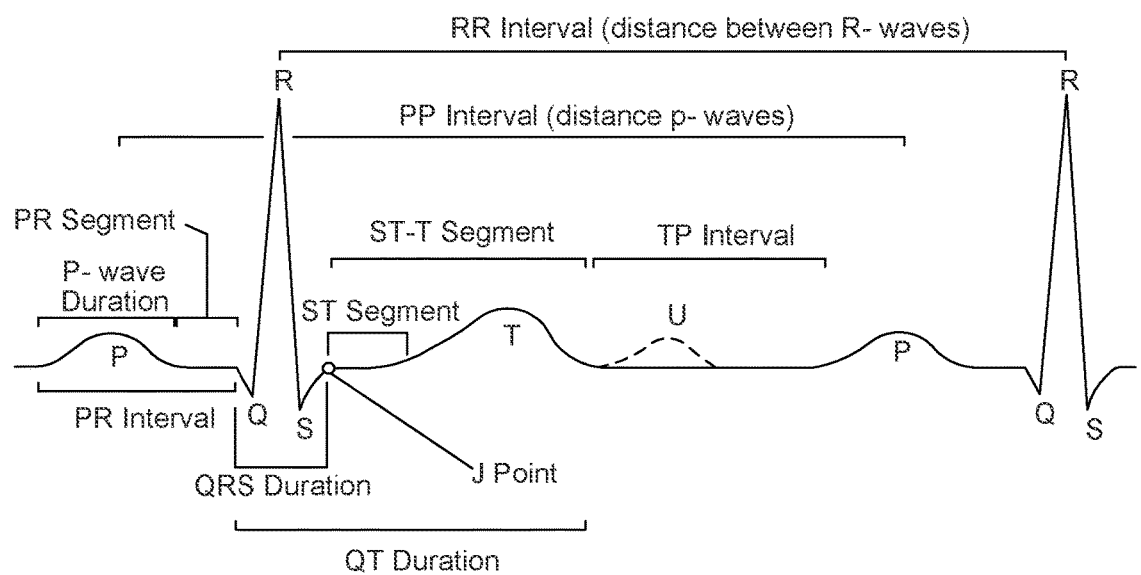
FIG. 2B illustrates a normal ECG waveform according to one or more embodiments.

FIG. 2B illustrates a normal ECG waveform according to one or more embodiments. A segment in an ECG is the region between two waves. PR segment starts at the end of the P wave and ends at the start of the QRS complex. The PR segment serves as a baseline (e.g., a reference line) of the ECG curve. The amplitude of any deflection/wave is measured by using the PR segment as the baseline. The ST segment starts at the end of the QRS wave and ends at the start of the T wave. The J point is the point where the ST segment starts and is used for determining an ST segment deviation (e.g., an elevation or depression). The TP segment is found between the end of the T-wave and the beginning of the next P-wave. A TP interval is the distance between the end of the T-wave and the onset of the next P-wave and may include a U-wave. An ST-T segment starts at the J point and ends at the end of the T-wave.

An interval in an ECG is a duration of time that includes one segment and one or more waves. The PR (or PQ) interval is a distance between the onset of the P-wave just prior to a QRS complex and the onset of the QRS complex. Thus, the PR interval starts at the start of the P wave and ends at the start of the QRS. It denotes the conduction of the impulse from the upper part of the atrium to the ventricle. The QRS interval covers the QRS complex from beginning to end and has a QRS duration. The QT interval starts at the start of the QRS and ends at the end of the T-wave. It denotes the electrical systole of the heart. A PP interval is a distance between consecutive P-waves. An RR interval is a distance between consecutive R-waves.

A P-wave represents atrial depolarization (activation) and has a P-wave duration from start to end. A Q-wave reflects ventricular septal depolarization. An R-wave is the first upward deflection after the P wave and part of the QRS complex. The R-wave represents resultant or major ventricular muscle depolarization. An S-wave of the QRS complex is a negative wave that follows the R-wave and represents basal ventricular depolarization. A T-wave represents ventricular repolarization. Additionally, sometimes the electrical activity of the ventricular papillary muscle is out of phase with the rest of the ventricles and will record as a U-wave that shows after the T-wave.

Figure 3:
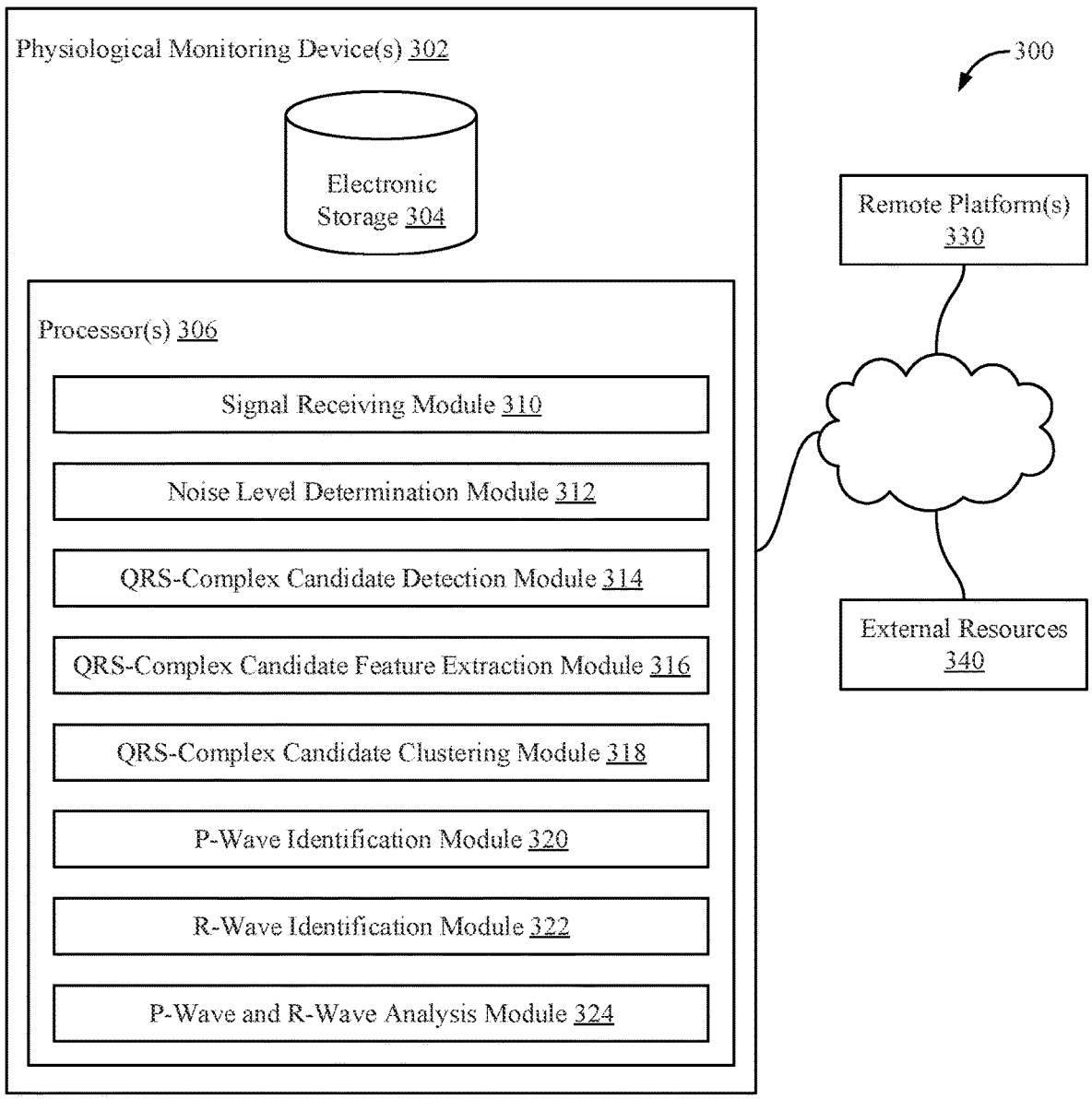
FIG. 3 is a schematic diagram of an exemplary physiological monitoring system for analyzing ECG waveforms according to one embodiment of the present disclosure.

FIG. 3 is a schematic diagram of an exemplary physiological monitoring system 300 configured to analyze ECG waveforms according to one embodiment of the present disclosure. As illustrated, the system 300 may include one or more components, for example, a physiological monitoring device 302 in wired or wireless connection with external resources 340 and remote platform(s) 330. In one embodiment, the physiological monitoring device 302, the remote platform(s) 330, and/or the external resources 340 may be operatively linked via one or more electronic communication links. Such electronic communication links may be established, at least in part, via a network such as the Internet and/or other networks or other communication media. Remote platform(s) 330 and external resources 340 may include medical devices (e.g., patient monitoring device or therapy device), one or more servers, a desktop computer, a laptop computer, a handheld computer, a tablet computing platform, a NetBook, a smartphone, and/or other platforms. For example, the physiological monitoring device 302 may receive ECG signals, analyze ECG waveforms, identify P-waves, and detect and classify heart block events. The analyzed ECG waveforms may be transmitted and stored in remote platform(s) 330 and external resources 340, for example, in a nurse station or in a patient's electronic medical record system. A detected low heart rate or identified heart block events may also trigger the monitoring device 302 to generate alarm signals that are transmitted to remote platform(s) 330 and external resources 340, for example, a hospital's alarm output system.

Figure 4:
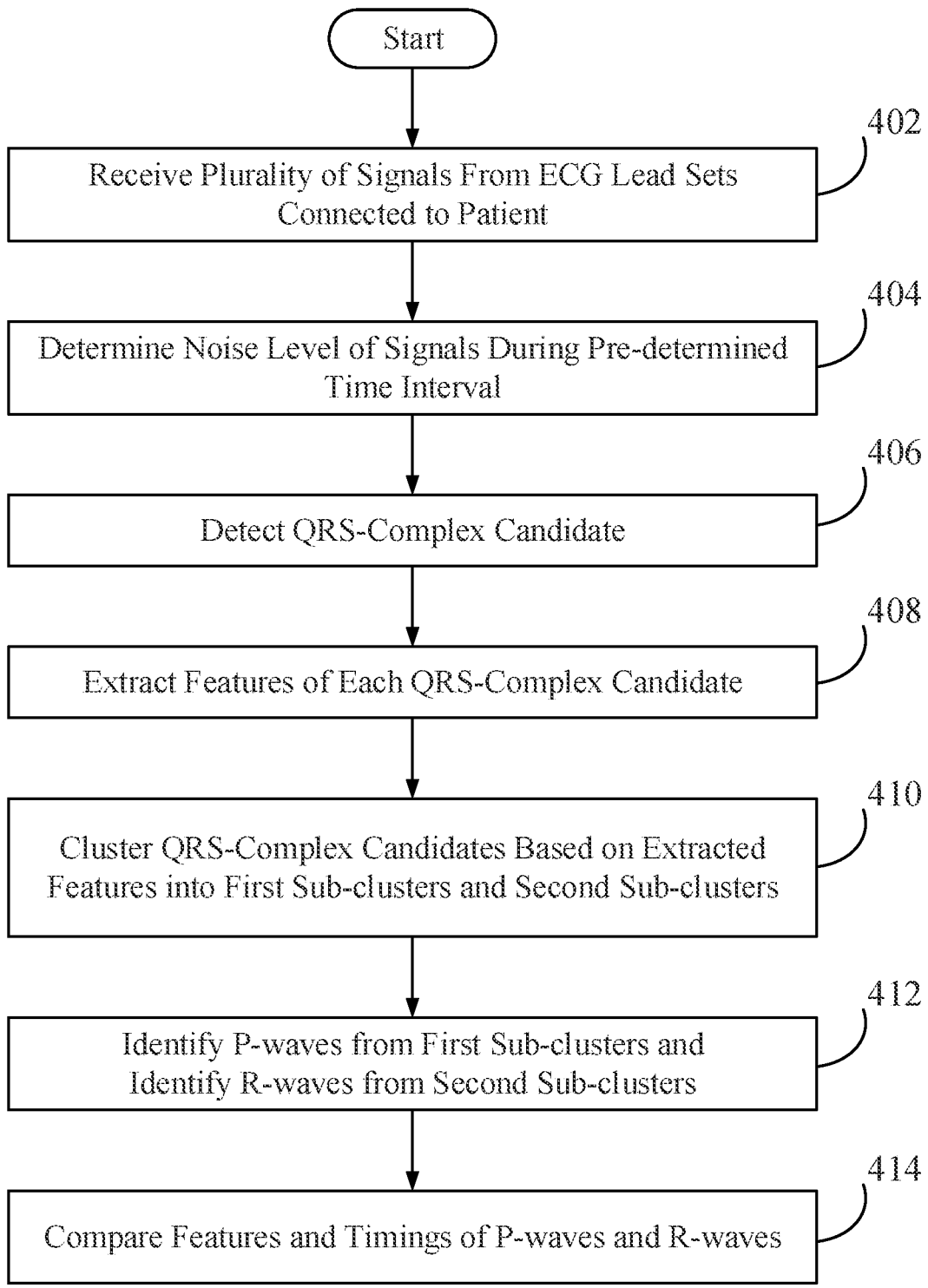
FIG. 4 is a flow diagram of an exemplary ECG waveform detection and analysis process according to one embodiment of the present disclosure.

One or more components of the system 300, e.g., physiological monitoring device 302 may be the same or similar as physiological monitoring device 7 illustrated in FIG. 1 and device 204 illustrated in FIG. 2A. Processor(s) 306 in the physiological monitoring device 302 may be configured to receive and analyze ECG waveforms, in accordance with FIG. 4 illustrating a flow diagram of an exemplary ECG waveform detection and analysis process. Physiological monitoring device 302 is capable of receiving physiological data (e.g., ECG signals) from a plurality of ECG leads connected to a patient. Processor(s) 306 may execute signal receiving module 310 and perform the signal receiving process 402 as illustrated in FIG. 4, where the received analog signals may be filtered via hardware and software filters 210 and 214 and converted into digital data stream via an A/D converter 212, in accordance with the embodiments illustrated in FIG. 2A.

Figure 5:
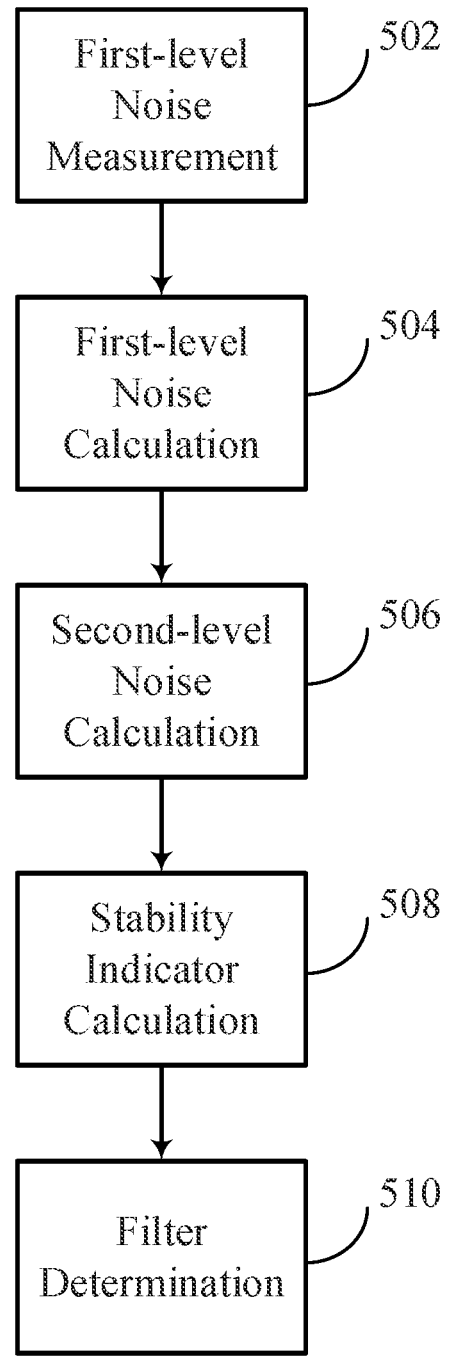
FIG. 5 is a flow diagram of an exemplary noise detection process according to one embodiment of the present disclosure.

Processor(s) 306 may further execute noise level determination module 312 and perform the noise determination process 404 as illustrated in FIG. 4. In one embodiment, the noise level of the received ECG signals may be dynamically determined, where the noise level may be used in subsequent ECG waveform analysis. FIG. 5 is a flow diagram of an exemplary noise detection process according to one embodiment of the present disclosure. As illustrated, the noise determination process 404 may include first-level noise measurement 502, first-level noise calculation 504 and a second-level noise measurement 506, where the two-level noise measurements may occur concurrently or sequentially. In one embodiment, the first-level noise measurement 502 may include a first-level noise calculation 504 performed by comparing a plurality of sample signals during a first pre-determined time interval that defines a block. Thus, the length of the first pre-determined time interval defines a block size or sample size of the block. For example, a range of about 10 to about 100 sample signals during a 40-400 millisecond (ms) interval may be compared, and a difference between a minimum value and a maximum value among the acquired samples may be determined as a first-level noise. In other words, the first-level noise is the peak-to-peak value between the largest maximum and the largest minimum within the pre-determined time interval. The first-level noise is then determined for the next first pre-determined time interval (i.e., for the next block) and so on. Thus, a first-level noise value is determined for each first pre-determined time interval or for each block. The first-level noise measurement may occur every 50 sample signals during an interval of approximately 200 ms. The time interval may be calculated as a time duration retrospectively from a most recent sample signal to earlier sample signals.

The noise determination process 404 further includes a second-level noise calculation 506 performed based on the first-level noise of a predetermined number M of consecutive first pre-determined time intervals or a predetermined number M of consecutive blocks, where M is an integer greater than two (e.g., 21 consecutive blocks). The second-level noise calculation may be performed at a regular second pre-determined time interval that is larger than the first pre-determined time interval. For example, the second pre-determined time interval may be performed every N first pre-determined time intervals, where N is an integer greater than one. The processor 306 is configured to refer to M first-level noise values determined from most recent M blocks for determining a second-level noise value and a stability indicator and update the second-level noise value and the stability indicator value each time the second-level noise calculation is performed (i.e., at every second pre-determined time interval).

Accordingly, the second pre-determined time interval used in the second-level noise calculation 506 may be different from the first pre-determined time interval used in the first-level noise measurement and calculation 502 and 504, respectively. In one embodiment, the second pre-determined time interval used in the second-level noise calculation 506 may be longer than the first pre-determined time interval used in the first-level noise calculation. For example, the first-level noise measurement and calculation may occur every 10-50 sample signals during an interval of approximately 40-200 ms, and the second noise measurement may occur every 30-150 sample signals during an interval of approximately 120-600 ms. That is, the second-level noise measurement may occur once every M consecutive first pre-determined time intervals, whereas the first-level noise measurement occurs for each first pre-determined time interval.

At least one of the first-level noise calculation 504 and second-level noise calculation 506 may be repeated at respective pre-determined time intervals. For example, within a time interval of 5 seconds, the first-level noise calculation 504 may repeat for a time block of approximately 40-200 ms, where a maximum and a minimum value of sample signals are collected within each time block, and a difference between the two extrema values is determined as first-level noise. The second-level noise calculation 506 may repeat for every 2-6 of such time blocks.

In order to calculate a second-level noise value, the processor 306 may rank or sort the plurality of first-level noise values obtained from the most recent M consecutive blocks, with the ranking being from lowest to highest. The processor 306 is then configured to calculate the second-level noise value and/or a stability indicator based on the ranked M first-level noise values (508 shown in FIG. 5). For example, the median value of the ranked M first-level noise values may be selected by the processor 306 as the second-level noise value. If M is an even number, then the median value is the lowest ranked middle ranked M first-level noise value. The processor 306 is further configured to calculate a stability indicator value based on the second-level noise value. In particular, the stability indicator value is the difference between the first-level noise value of the lowest ranked block (i.e., the smallest first-level noise value of the M first-level noise values) and the second-level noise value (i.e., the median first-level noise value of the M first-level noise values). Each time the second-level noise is calculated (i.e., every second pre-determined time interval), the M first-level noise values are updated to discard the oldest first-level noise values and factor in the most recent first-level noise values acquired since that last second-level noise calculation. Once updated, the M first-level noise values are again ranked or resorted in order to calculate (update) the second-level noise value and the stability indicator value.

In one embodiment, within a time interval of 5 seconds, the first-level noise calculation 504 may be consecutively performed during a time block of 200 ms and repeated for 25 times. A first-level noise may be calculated for each time block. The second-level noise calculation 506 may be consecutively performed during a second pre-determined time interval of 600 ms and repeated for 8 times. For each 600 ms pre-determined time interval, all first-level noises calculated from each 200 ms time block (M=25) are ranked from the minimum noise level to the maximum noise level with a middle-ranked noise level (median noise level) substantially equidistant therebetween. The second-level noise may be calculated, for example, as the noise level of the median noise level of the ranked 200 ms time blocks (i.e., of the ranked first-level noise values). Optionally, the stability indicator value may also be calculated, for example, as a difference between the minimum and the median-ranked noise level of the ranked 200 ms time blocks. It should be noted that the aforementioned embodiments are for exemplary purposes without limiting the scope of the present disclosure. The time interval for signal analysis can be in a range of 1-10 seconds. The time block for the first-level noise calculation 504 can be in a range of 40-200 ms, and the time block for the second-level noise calculation 506 in a range of 80-1200 ms.

The multi-level noise measurement according to the aforementioned embodiments in the present disclosure provides advantages including improvements in detection sensitivity. By calculating noise on a two-level basis, for example, using different time intervals and updating noise values by ranking, the two-level noises and stability indicator are updated in a real-time manner, and can be used to determine the bandwidth of a series of filters used in analyzing ECG waveforms (e.g., QRS complex and P-waves) and/or extracting features from the ECG waveforms with high accuracy (see step 510 in FIG. 5).

For example, the first-level noise is used for the determination of the second-level noise (i.e., the iso-line noise, baseline noise). When the iso-line noise level is below a predetermined noise threshold, the original ECG signal with bandwidth 0.5-40 Hz is used for measuring the morphology features of the QRS-complex candidate. Otherwise, when the iso-line noise level (i.e., the second-level noise) is above a predetermined noise threshold with the stable status, a low-pass 10 Hz filter is applied to the ECG signal with bandwidth 0.5-40 Hz, and the output waveform with bandwidth 0.5-10 Hz is used for measuring the morphology features of the QRS-complex candidate. A stable status occurs when the stability indicator value is less than a predetermined stability threshold value. In other words, when a second-level noise value is greater than a predetermined noise threshold, the processor 306 is configured to adjust a filter setting of a low-pass filter that is applied to the ECG signal to filter out a greater level of noise so that target features of the ECG signal are capable of being detected.

An unstable status occurs when the stability indicator value is equal to or greater than the predetermined stability threshold value. When the iso-line noise level (i.e., the second-level noise) is above a predetermined noise threshold with the unstable status, a low pass 10 Hz filter is still applied to the original ECG signal with bandwidth 0.5-40 Hz. A further beat level noise level including high frequency and low frequency is assessed to determine if this candidate beat is an artifact (excluded), or if it is still to be used for measuring the morphology features as a QRS-complex candidate against a predetermined high frequency noise threshold and a predetermined low frequency noise threshold. In other words, additional filter settings may be configured and applied to the ECG signal when the stability indicator value is indicative of an unstable status, including low pass filter settings and high pass filter settings.

A QRS complex is the combination of three waves in the ECG waveform corresponding to the depolarization of the right and left ventricles of the human heart and contraction of the large ventricular muscles. The three waves include the Q-wave, the R-wave, and the S-wave noted above. With a large amplitude and a small width, the R-wave (a sharp upward deflection) in the QRS complex is suitable for measuring heart rate. The amplitude may be measured relative to the PR segment amplitude, used as a baseline. The width of the R-wave may be the QRS duration, whereas the width of a P-wave may be the P-wave duration.

The features in the morphology of the detected QRS complexes may also be extracted from the ECG waveform in the selected filter bandwidth based on the determined second noise level and the stability indicator value. The extracted features may include but not limited to peak fiducial time, amplitude, width, and peak curvature. For example, processor(s) 306 may execute QRS-complex candidate feature extraction module 316 and extract features of the detected QRS-complex candidates (see e.g., process 408 in FIG. 4). To detect a QRS-complex candidate, the processor(s) 306 is configured to detect signal peaks within an ECG signal and compare the values of the detected signal peaks to a QRS-complex candidate threshold value. Those signal peaks that are equal to or greater than the QRS-complex candidate threshold are detected as QRS-complex candidates, while those signal peaks that are less than the QRS-complex candidate threshold are not identified as QRS-complex candidates.

In order to extract a feature of a QRS-complex candidate, for example, the peak curvature feature, at least one of the second-level noise and the stability indicator may be used to determine the bandwidth of a series of filters applied to the ECG signals to reduce excessive noise which distorts the peak sharpness of R-waves in the QRS-complex candidates.

An R-wave is typically the peak wave in the ECG waveform. When a patient has a normal cardiac condition, an R-wave has a sharp morphology with a large amplitude and small width, while the preceding P-wave has a small amplitude (e.g., lower than 0.25 mV detected by ECG lead II) and small width (e.g., less than 120 ms in duration) Therefore, a P-wave can be easily differentiated from an R-wave. Additionally, each R-wave in the QRS complex is preceded by one P-wave. However, the morphological features of P-waves, including amplitude and width, can be substantively changed by cardiac abnormalities including heart block events. For example, the presence of left atrial hypertrophy may cause the P-wave to have increased amplitude and prolonged duration as well as substantive notching, while the presence of right atrial hypertrophy may cause the P-wave to have significantly increased amplitude where the P-wave becomes the peak wave in the ECG waveform instead of the R-wave. In some other cases, P-wave does not have a 1:1 correspondence with R-wave. That is, one or more beats are missed.

As a result, when cardiac abnormalities exist, a P-wave could exceed the QRS-complex candidate threshold value and be mistaken for an R-wave of a QRS complex. Thus, in some cases, a P-wave with large amplitude is initially detected as QRS-complex candidates because of the abnormal P-R timing or due to an absence of R-waves caused by an AV conduction block. These large P-waves might not be rejected effectively, and mistakenly detected as valid ventricular R-waves. Consequently, anticipated heart rate related alarms (brady, pause and asystole) may be missed.

Accordingly, a QRS-complex candidate could be a true QRS-complex with an R-wave or could be a false QRS-complex that is actually a P-wave. Processor 306 is configured to detect QRS-complex candidates in an ECG waveform and validate whether each QRS-complex candidate includes an R-wave or a P-wave, for example, by clustering those QRS-complex candidates that meet QRS-complex or R-wave criteria as validated QRS-complexes and clustering those QRS-complex candidates that do not meet QRS-complex or R-wave criteria or those that meet P-wave criteria as P-waves. The processor 306 may then process each cluster for analyzing R-waves and P-waves for measuring a heartbeat and detecting heart block events, respectively.

Accordingly, when processor(s) 306 detect QRS-complex candidates in a pre-determined time interval (e.g., 3-30 seconds), and extract one or more features of each detected QRS-complex candidate, it is important to differentiate abnormal P-waves from R-waves. In one embodiment of the present disclosure, processor(s) 306 may further cluster the detected QRS-complex candidates based on one or more extracted features of each candidate (see e.g., module 318 as illustrated in FIG. 3 and process 410 in FIG. 4). For example, the detected QRS-complex candidates may be clustered into two clusters based on the amplitude feature of each QRS-complex candidate, where one cluster includes a plurality of QRS-complex candidates having a larger mean amplitude than that of another cluster. Without limitation, the extracted features used for clustering detected QRS-complex candidates may include amplitude, width, peak fiducial time, peak curvature, or any combinations thereof.

In essence, with two clusters of QRS-complex candidates, the processor 306 is configured to determine which cluster corresponds to a "big" rhythm (ventricular rhythm) as R-waves and which cluster corresponds to a "small" rhythm (potential P-waves). The big rhythm corresponds to the cluster for which the amplitude is stable and which has the higher mean peak-to-peak amplitude. The small rhythm cluster is another cluster, for which the amplitude is stable and has the lower mean peak-to-peak amplitude.

Next, the processor 306 is configured to compare features of the first cluster of QRS-complex candidate with those of the second cluster of QRS-complex candidates in order verify that the smaller rhythm is actually the atrial rhythm and that the big rhythm is the ventricular rhythm for an ECG lead. For this to be true, all of the following conditions must hold: the mean peak curvature of the big rhythm (e.g., of the second cluster) must be higher than the mean peak curvature of the small rhythm (e.g., of the first cluster); the mean peak-to-peak amplitude of the small rhythm must not exceed a maximum P-wave amplitude, considered to be equal to 0.4 mV, for example; and a mean width of the small rhythm must exceed the minimum width threshold of 40 ms, for example.

In one embodiment, one or more pre-determined thresholds may be established for attributing each QRS-complex candidate to designated clusters. The pre-determined thresholds may be manually configured or automatically determined based on the features of previously collected ECG data which may include the existing clusters. For example, an amplitude threshold (e.g., 0.1-0.4 mV) may be pre-determined to attribute each QRS-complex candidate. Alternatively, the amplitude threshold may be dynamically determined as a mean amplitude of one cluster. When a QRS-complex candidate is detected, its amplitude may be compared with the pre-determined threshold. When the amplitude exceeds the threshold, this QRS-complex candidate may be attributed to one cluster and the mean amplitude of this cluster and/or the amplitude threshold may be dynamically updated. When the amplitude does not exceed the threshold, the QRS-complex candidate may be attributed to another cluster where the mean amplitude of such cluster may be dynamically updated.

In another embodiment, each cluster has a pre-determined amplitude threshold, as an average amplitude (AVG) of all existing QRS-complex candidates within its cluster. When a new QRS-complex candidate is introduced, its amplitude may be compared with the average amplitude of each cluster. When the amplitude of the new candidate exceeds the AVG or is within a certain range of the AVG (e.g., 30% AVG-200% AVG, 50% AVG-150% AVG, 80% AVG-120% AVG), this candidate may be added into the current cluster, and the AVG of that cluster may be dynamically updated to account for the new candidate.

As such, all QRS-complex candidates detected within a pre-determined time interval may be attributed into different clusters based on their extracted morphological features. This clustering process may also be repeated for multiple pre-determined time intervals. All clusters and their corresponding features (e.g., mean amplitude, mean width, and mean peak curvature) are updated in real-time as new QRS-complex candidates are added to a respective cluster. As mentioned above, the threshold values may also be updated in real-time to be compared with a new QRS-complex candidate. As will be described, such clustering process can be used by processor(s) 306 to differentiate P-waves from R-waves even when heart block events occur, preventing P-waves with large amplitudes from being mistakenly identified as R-waves.

The aforementioned embodiments including two clusters are for exemplary purposes, without limiting the scope of the present disclosure. More clusters may be established based on the extracted features of the detected QRS-complex candidates as needed. For example, a QRS-complex candidate may not qualify to be attributed to any of the established clusters. Such candidate may be rejected from the two clusters and/or attributed to a third cluster for further analysis. Additionally, or alternatively, the size of each cluster can be adjusted as needed. For example, during a pre-determined time interval, each cluster may be limited to include 2-30 QRS-complex candidates. When the number of QRS-complex candidates within the cluster reaches its upper limit, one existing QRS-complex candidate may be removed from its corresponding cluster such that a new candidate can be added. Without limiting the scope of the present disclosure, the removal of an existing QRS-complex candidate can be based on the timing, for example, a QRS-complex candidate with an earliest timing may be firstly removed from its corresponding cluster in a first-in-first-out (FIFO) methodology. Alternatively, the removal can be based on the extracted features of the QRS-complex candidate, for example, when all existing QRS-complex candidates within the clusters are ranked by features (amplitude, width, peak curvature, etc.), a QRS-complex candidate with a lowest ranking may be firstly removed from the cluster.

The present disclosure may further identify and validate different clusters based on the features of the QRS-complex candidates within the clusters, thereby improving the accuracy in separating P-waves from R-waves and identifying heart block events. In one embodiment, processor(s) 306 may identify and validate P-waves and/or R-waves by comparing the features of the QRS-complex candidates within different clusters (see e.g., modules 320 and 322 in FIG. 3, and process 412 in FIG. 4). For example, when a first cluster has a mean amplitude smaller than that of a second cluster, the QRS-complex candidates within the first cluster may be identified as P-waves, while the QRS-complex candidates within the second cluster identified as R-waves. Thus, processor(s) 306 is configured to validate that the QRS-complex candidates of the second cluster are QRS-complexes that include respective R-waves and that QRS-complex candidates of the first cluster include respective P-waves and, thus, are not QRS-complexes.

The identification of P-waves and R-waves within different clusters may further include the validation process by comparing the features of the clusters. For example, when a first cluster has been identified to include P-waves and a second cluster to include R-waves, one or more features of the two clusters may further be compared, including mean amplitude, mean width, or mean peak curvature of each cluster, or any combinations thereof. The P-waves identified in the first cluster and/or the R-waves identified in the second cluster may be validated, respectively, when one or more of the following conditions are satisfied. The mean amplitude of the first cluster may be smaller than or equal to that of the second cluster. The mean amplitude of the first cluster may be smaller than or equal to a pre-determined threshold, where the pre-determined threshold may be in a range of e.g., 0.3 mV-0.5 mV. The mean width (i.e., duration) of the first cluster may be larger than or equal to a pre-determined threshold, where the threshold may be in a range of e.g., 20 ms-60 ms. The mean peak curvature of the first cluster may be lower than that of the second cluster. That is, the peak curvature of the first cluster may be smoother than that of the second cluster. The validation of P-waves and R-waves may further improve the accuracy in differentiating P-waves with a large amplitude from R-waves even when heart block events occur. As such, the identified R-waves without being mistakenly mixed with P-waves can be used to accurately calculate heart rate. Furthermore, the validated P-waves and R-waves in the clusters can be further used to evaluate and identify different types of heart block events, as described in more details in accordance with FIG. 6.

Depending on the extent of electrical signal impairment, a heart block can be further categorized into different types. Some types of heart block do not need substantive treatment while other types indicate serious cardiac conditions where the patient needs to be treated with a pacemaker. Accordingly, in one embodiment, when the P-waves and R-waves attributed in different clusters are identified, processor(s) 306 may further analyze the identified P-waves and R-waves by comparing the features and/or timings of the P-waves and R-waves, so as to detect and identify the types of the heart block events (see e.g., module 324 in FIG. 3 and process 414 in FIG. 4). For example, a P-P interval between two P-waves may be calculated using P-waves in the first cluster. An R-R interval between two R-waves may be calculated using R-waves in the second cluster. Furthermore, the timings of P-waves in the first cluster and the timings of R-waves in the second cluster may further be analyzed and compared to calculate a peak-to-peak P-R interval (i.e., a time duration between a peak of a P-wave and a peak of a corresponding R-wave). One or more of the calculated features and/or timings can be used to determine the types of heart block events. Typically, an R-wave is dependent on a preceding P-wave. Thus, it can be said that an R-wave linked to a preceding P-wave is a corresponding R-wave. However, during certain heart block events, a link or dependency between a P-wave and an R-wave can become disconnected to the point where the P-wave and R-wave are independent of each other. In this case, it can be said that a P-wave does not have a corresponding R-wave. Furthermore, in some cases such as when a P-wave asystole is present, R-waves may not be present at all.

Figure 6:
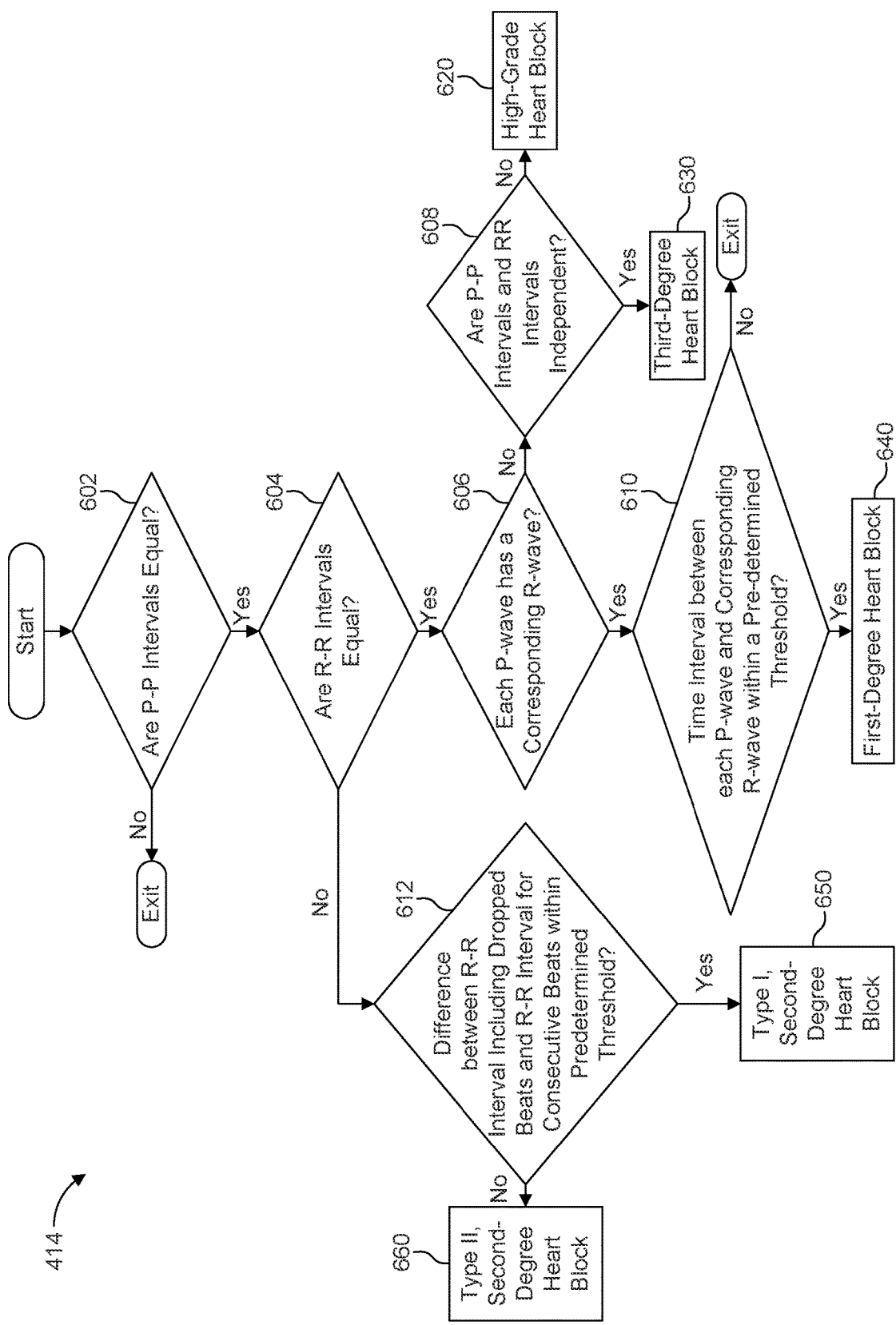
FIG. 6 is a flow diagram of an exemplary ECG waveform analysis process according to one embodiment of the present disclosure.

FIG. 6 is a flow diagram of an exemplary ECG waveform analysis process according to one embodiment of the present disclosure. The ECG waveform analysis is implemented by processor(s) 306 to detect P-waves and R-waves, distinguish P-waves from R-waves, detect and classify heart block events, output results on a display 4, and generate one or more alarms based on different types of detected heart block events. During a pre-determined time interval (e.g., 5-20 seconds, 2-30 seconds, 10-40 seconds), one or more of P-P intervals, R-R intervals, and P-R intervals may be calculated and compared in order to identify different types of heart block events. For example, two or more of the P-P intervals within the first cluster may be compared (see step 602). For example, a first P-P interval calculated from a first two consecutive P-waves may be compared with a second P-P interval calculated from a second two consecutive P-waves.

When the P-P intervals are not equal or not substantially equal (N in step 602), the P-waves may indicate the presence of other cardiac conditions and therefore be rejected for further analysis of heart block events. When the P-P intervals are equal or substantially equal (Y in step 602), two or more R-R intervals within the second cluster may be compared (see step 604). For example, a first R-R interval calculated from a first two consecutive R-waves may be compared with a second R-R interval calculated from a second two consecutive R-waves.

When the R-R intervals are determined to be substantially equal (Y in step 604), the timings of P-waves within the first cluster and R-waves within the second cluster may further be compared to determine whether each P-wave has a corresponding R-wave (step 610), and to calculate P-R interval. Here, "substantially equal" means that the values being compared are within an acceptable predetermined margin of each other (e.g., within 5% or 10% of each other).

During the pre-determined time interval, if each P-wave has a corresponding R-wave (Y in step 610), and the P-R interval is within a pre-determined threshold range (Y in step 610), first-degree heart block may be identified (step 640). The pre-determined threshold range may be e.g., 100-700 ms, 150-600 ms, or 200-500 ms. A first-degree heart block occurs when the electrical impulse still reaches the ventricles but moves more slowly than normal through the AV node. When the P-R interval is out of a pre-determined threshold range (N in step 610), the current P-wave may be rejected for further analysis of heart block events.

When the R-R intervals are determined to be unequal or not substantially equal (N in step 604), a different type of heart block (e.g., second-degree heart block) may be identified. In some cases, R-R intervals may have progressive decrease during the pre-determined time interval. In other cases, a substantive portion of R-R intervals may be equal, yet one or more heartbeats (QRS complex) are dropped from the ECG waveform which causes a larger R-R interval. An R-R interval including dropped heartbeats and an R-R interval for consecutive heartbeats may be calculated, respectively.

Additionally, different subtypes of second-degree heart blocks may be identified by calculating a difference between a R-R interval including dropped heartbeats and a R-R interval for consecutive heartbeats and comparing such difference with a pre-determined threshold (see e.g., step 612). For example, when the R-R interval including dropped beats is less than twice of the R-R interval including consecutive beats, a Type I second-degree heart block may be identified (step 650). Otherwise, a Type II second-degree heart block may be identified (step 660).

Alternatively, or additionally, other features extracted from one or more of P-P intervals, R-R intervals, and P-R intervals may also be utilized to identify different subtypes of second-degree heart blocks. For example, when R-R intervals have a progressive decrease during the pre-determined time interval and the R-R interval including dropped beats is less than twice of the R-R interval including consecutive beats, a Type I second-degree heart block may be identified. When a substantive portion of R-R intervals is equal and the R-R interval including dropped beats is twice of the R-R interval including consecutive beats, a Type II second-degree heart block may be identified.

In some cases, each P-wave during the pre-determined time interval may not have a corresponding R-wave (N in step 606). For example, during a total heart block event, the pathway is cut off. Thus, the link between P-waves and R-waves is disconnected such that R-waves are independent of P-waves. Accordingly, P-P intervals calculated from P-waves within the first cluster may further be compared with R-R intervals calculated from R-waves within the second cluster. When R-R intervals are at least partially related with P-P intervals during the pre-determined time interval (N in step 608), for example, the R-R intervals are at least twice of the P-P intervals in consistent manners, a high-grade heart block may be identified (see step 620). In an embodiment, an R-R interval may be N times that of a P-P interval (N ≥ 2, and N is an integer), with a variation range of e.g., 0.5%-20%. When P-P intervals and R-R intervals are determined to be independent from each other (Y in step 608), meaning R-R intervals are not integer multiples of P-P intervals, a third-degree heart block (i.e., a total heart block) may be identified (see step 630).

Alternatively, or additionally, the identified P-waves and R-waves in different clusters may further be analyzed for identifying different types of heart block events. For example, when P-P intervals and R-R intervals are independent without corresponding relationships, R-waves in the second clusters may further be analyzed to determine the heart rate. When the heart rate is lower than a pre-determined threshold in a range of e.g., 60-90 beats per minute (bpm), a third-degree heart block may be identified.

The present disclosure provides the identification of P-waves in real time and correspondingly, different types of heart block events in accurate and effective manners. The noise determination process may be used to determine the bandwidth of a series of filters used for subsequent noise reduction from ECG signals and feature extraction of the ECG waveforms. Thus, one or more features may be extracted from each QRS-complex candidate based on the determined noise level of the received ECG signals by, for example, configuring filter settings used for feature extraction according to the determined noise level. The clustering of QRS-complex candidates based on the extracted features may facilitate the identification of P-waves and R-waves. When the P-waves and R-waves are identified in different clusters, by comparing their features and/or timings, different types of heart block events can be identified in accurate and timely manner. As such, when heart block events occur, P-waves with large amplitude can be prevented from being mistakenly identified as R-waves. The heart rate based on R-waves may also be precisely calculated by the physiological patient monitor. When heart block events occur, the physiological patient monitor is capable of detecting the low heart rate, generating heart-rate related alarms, and reporting heart block events.

Figure 7:
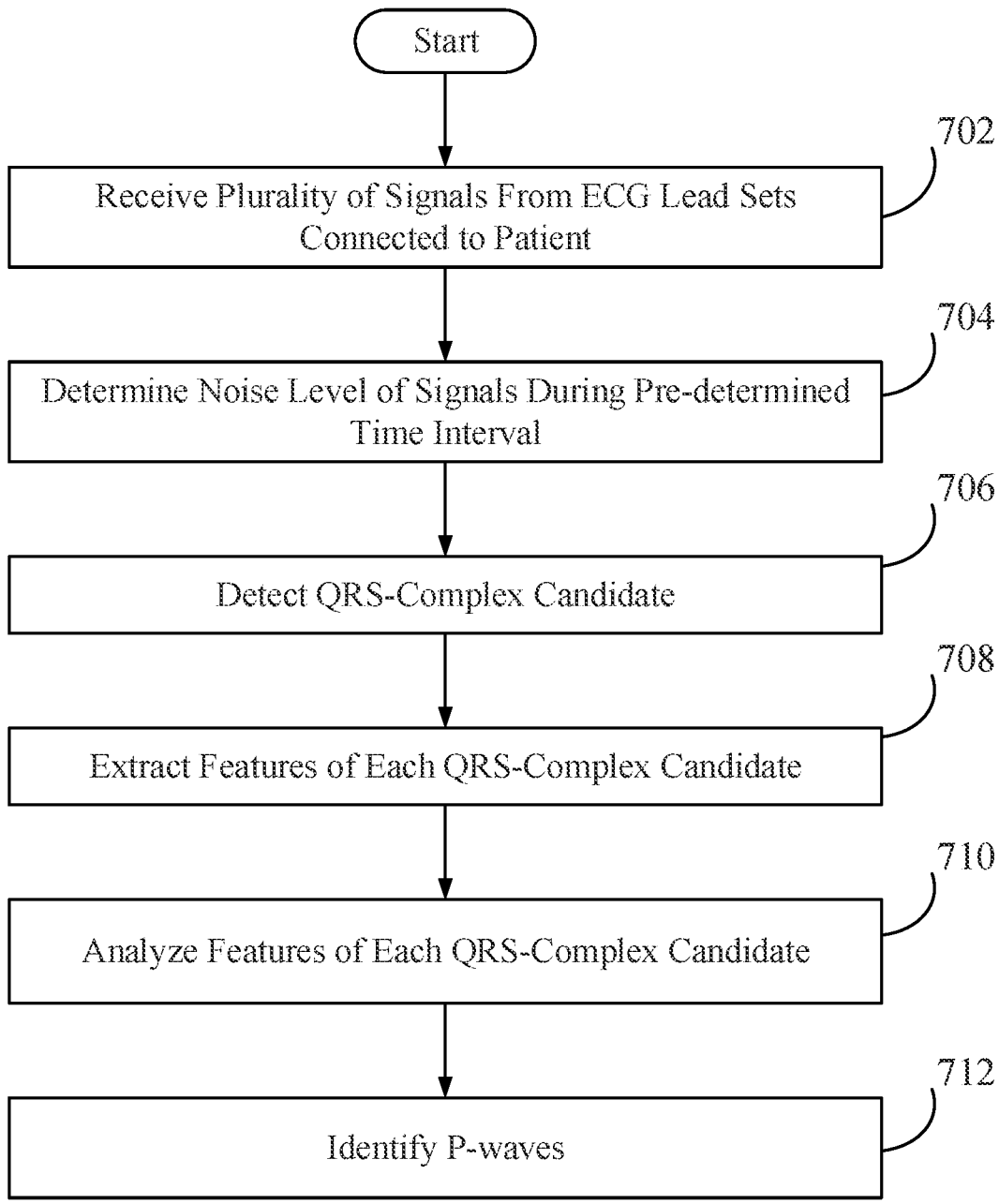
FIG. 7 is a flow diagram of an exemplary ECG waveform analysis process according to one embodiment of the present disclosure.

In certain clinical conditions, a patient may have P-wave asystole (also called ventricular asystole). During this clinical condition, P-waves are present in the ECG waveforms while R-waves are missing and are not present at all. In accordance with FIG. 7, processor(s) 306 may identify P-waves and detect and report the absence of R-waves without mistakenly treating P-waves as R-waves. As illustrated in steps 702, 704, 706 and 708 which are similar to steps 402, 404, 406 and 408, respectively, the ECG signals that are received from a plurality of ECG leads connected to a patient may be used to determine the noise level and detect QRS-complex candidates. One or more features of each QRS-complex candidate may be extracted and further analyzed to identify P-waves even in the absence of R-waves (see steps 710 and 712).

In accordance with FIG. 3, processor(s) 306 in the physiological monitoring device 302 may execute QRS-complex candidate feature extraction module 316 as well as P-Wave and R-Wave analysis module 324, thereby extracting and analyzing the detected QRS-complex candidates. The analyzed features may include one or more of amplitude, width, peak fiducial time, peak curvature, and peak-to-peak interval. Upon analyzing consecutive QRS-complex candidates detected in a pre-determined time interval, for example, a P-wave asystole may be identified when one or more of the following conditions are satisfied. For the consecutive QRS-complex candidates, the amplitude of each candidate is substantively equal or within a pre-determined range of variation (e.g., ≤5%, ≤10%, ≤15%, ≤20%, ≤25%, ≤30%). The amplitude of each QRS-complex candidate is lower than a pre-determined threshold, where the threshold is a range of e.g., 0.2-0.5 mV. The width of each consecutive QRS-complex candidate is substantively equal or within a pre-determined range of variation (e.g., ≤5%, ≤10%, ≤15%, ≤20%, ≤25%, ≤30%). The width of each consecutive QRS-complex candidate is with a pre-determined range, for example, 20 ms-180 ms. The peak curvature of each consecutive QRS-complex candidate is lower than a pre-determined threshold, where the threshold is in a range of e.g., 20-80 units. The peak-to-peak interval between two consecutive QRS-complex candidate is substantively equal or within a pre-determined range of variation (e.g., ≤5%, ≤10%, ≤15%, ≤20%, ≤25%, ≤30%). Optionally, the noise level determined in step 702 may also be analyzed to determine whether the consecutive QRS-complex candidates are stable with low peak-to-peak noise. As such, the consecutive QRS candidates may be identified as P-waves without being treated as R-waves. Accordingly, the physiological monitoring device 302 may report the absence of R-waves and/or generate heart-rate related alarms, for example, reporting asystole.

It should be noted that one or more of the steps 402, 404, 406, 408, 410, 412 and 414 in FIG. 4 may be used, where the numbers and/or orders of the steps are for exemplary purposes, and not intended to limit the scope of the disclosure. It should be noted that one or more of the steps 502, 504, 506, 508 and 510 in FIG. 5 may be used, where the numbers and/or orders of the steps are for exemplary purposes, and not intended to limit the scope of the disclosure. It should also be noted that one or more of the steps 602, 604, 606, 608, 610 and 612 may be used to determine different types of heart block events (620, 630, 640, 650 and 660) as illustrated in FIG. 6, where the numbers and/or orders of the steps are for exemplary purposes, and not intended to limit the scope of the disclosure. It should also be noted that one or more of the steps 702, 704, 706, 708, 710 and 712 in FIG. 7 may be used, where the numbers and/or orders of the steps are for exemplary purposes, and not intended to limit the scope of the disclosure.

It is also contemplated that the implementation of the components of the present disclosure can be done with any newly arising technology that may replace any of the above implementation technologies.

In general, it is contemplated by the present disclosure that the physiological monitoring device and the monitor mount (e.g., device 7 and device mount 10 as illustrated in FIG. 1, device 204 as illustrated in FIG. 2A, and device 302 as illustrated in FIG. 3) include electronic components or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in the physiological monitoring device and the monitor mount (e.g., device 7 and device mount 10 as illustrated in FIG. 1, device 204 as illustrated in FIG. 2A, and device 302 as illustrated in FIG. 3) may be adapted to execute any operating system, including Linux, UNIX, Windows Server, etc., as well as virtual machines adapted to virtualize execution of a particular operating system, including customized and proprietary operating systems. The physiological monitoring device and the monitor mount are further equipped with components to facilitate communication with other computing devices over one or more network connections, which may include connections to local and wide area networks, wireless and wired networks, public and private networks, and any other communication network enabling communication in the system.

By way of example, hardware processors described in the present disclosure (e.g., processor(s) 3 and 12 as illustrated in FIG. 1 and processor(s) 306 as illustrated in FIG. 3) are used for controlling the general operations of a physiological monitoring device (e.g., device 7 as illustrated in FIG. 1, device 204 as illustrated in FIG. 2A, and device 302 as illustrated in FIG. 3). Each one of the one or more processors can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing devices capable of executing any type of instructions, algorithms, or software for controlling the operation and performing the functions of the physiological monitoring device.

Hardware processors described in the present disclosure (e.g., processor(s) 3 and 12 as illustrated in FIG. 1 and processor(s) 306 as illustrated in FIG. 3) may also be configured to execute modules by software, hardware, firmware, or any combinations thereof, and other mechanisms for configuring processing capabilities on the processors. As described in the present disclosure, "module" may refer to any component or set of components that perform the functionality attributed to the module. It may include one or more physical processors during execution of processor-readable instructions, circuitry, hardware, storage media, and/or any other components.

By way of another example, memory described in the present disclosure (e.g., memory 8 and 13 as illustrated in FIG. 1, and electronic storage 304 as illustrated in FIG. 3) can be a single memory or one or more memories or memory locations that include, but are not limited to, a random access memory (RAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy. The memory 8 can be used to store any type of instructions and patient data associated with algorithms, processes, or operations for controlling the general functions and operations of the physiological monitoring device.

Additionally, the electronic device (e.g., physiological monitoring device 7 and monitor mount 10 as illustrated in FIG. 1, device 204 as illustrated in FIG. 2A and device 302 as illustrated in FIG. 3) includes a display/GUI. As illustrated in FIG. 1, for example, the display/GUI 4 is for displaying various patient data and hospital or patient care information and includes a user interface implemented for allowing communication between a user and the physiological monitoring device 7. The display/GUI 4 includes, but is not limited to, a keyboard, a liquid crystal display (LCD), cathode ray tube (CRT), thin film transistor (TFT), light-emitting diode (LED), high definition (HD) or other similar display devices with touch screen capabilities. The patient information displayed can, for example, relate to the measured physiological parameters of the patient 1 (e.g., blood pressure, heart related information, pulse oximetry, respiration information, etc.) as well as information related to the transporting of the patient 1 (e.g., transport indicators).

A computer-readable medium can comprise DRAM, RAM, ROM, EEPROM, CD-ROM, or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, include compact disc (CD), laser disc, optical disc, digital versatile disc (DVD), floppy disk and Blu-Ray™ disc where disks usually reproduce data magnetically, while discs reproduce data optically with lasers. Combinations of the above are also included within the scope of computer-readable media.

The detailed description is made with reference to the accompanying drawings and is provided to assist in a comprehensive understanding of various example embodiments of the present disclosure. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments. In addition, descriptions of well-known functions and constructions may be omitted for clarity and conciseness. Accordingly, those of ordinary skill in the art will recognize that various changes and modifications of the examples described herein can be made without departing from the spirit and scope of the present disclosure.

Use of the phrases "capable of," "capable to," "operable to," or "configured to" in one or more embodiments, refers to some apparatus, logic, hardware, and/or element designed in such a way to enable use of the apparatus, logic, hardware, and/or element in a specified manner. Use of the phrases "substantially equal" in one or more embodiments, refers to the variation is smaller than or equal to e.g., 1%, 2%, 5%, 7%, 10%, 15%, 18%, 20% or 25%. Use of the phrases "about" or "approximate" in one or more embodiments, refers to the variation is smaller than or equal to e.g., 1%, 2%, 5%, 7%, 10%, 15%, 18%, 20% or 25%. The subject matter of the present disclosure is provided as examples of apparatus, systems, methods, circuit, and programs for performing the features described in the present disclosure. However, further features or variations are contemplated in addition to the features described above. It is contemplated that the implementation of the components and functions of the present disclosure can be done with any newly arising technology that may replace any of the above implemented technologies.

Various modifications to the disclosure will be readily apparent to those skilled in the art, and the generic principles defined herein may be applied to other variations without departing from the spirit or scope of the present disclosure. Throughout the present disclosure the terms "example," "examples," or "exemplary" indicate examples or instances and do not imply or require any preference for the noted examples. Thus, the present disclosure is not to be limited to the examples and designs described herein but is to be accorded the widest scope consistent with the principles and novel features disclosed.

What is claimed is:

1. A system comprising:
one or more processors configured to:

receive an ECG signal from an ECG lead configured to be connected with a patient;
acquire a plurality of samples from the ECG signal;
determine a noise level of the plurality of samples;
identify a plurality of QRS-complex candidates from the ECG signal;
extract one or more features from each QRS-complex candidate based on the determined noise level of the plurality of samples;
cluster the plurality of QRS-complex candidates into at least two clusters based on the one or more features extracted from each QRS-complex candidate;
identify the one or more P-waves from the clustered plurality of QRS-complex candidates in real-time; and
generate a heart-rate related alarm based on the identified one or more P-waves.

2. The system of claim 1, wherein the one or more processors is further configured to determine the noise level of the plurality of signals samples by measuring a plurality of first noise levels for a plurality of first predetermined time intervals that are consecutive to each other, wherein each of the plurality of first noise levels corresponds to a respective first predetermined time interval such that each of the plurality of first noise levels is measured over a duration of a different one of the plurality of first predetermined time intervals.

3. The system of claim 2, wherein the each of the plurality of first noise levels is a difference between a maximum value and a minimum value of the samples acquired during its respective first predetermined time interval.

4. The system of claim 2, wherein the one or more processors is configured to rank the plurality of first noise levels from lowest to highest, determine a median value of the ranked plurality of first noise levels as a second noise level, and configure at least one filter used for extracting the one or more features from each QRS-complex candidate based on the second noise level.

5. The system of claim 4, wherein the one or more processors is configured to calculate a difference between a lowest-ranked first noise level of the plurality of first noise levels that represents a smallest first noise level and the median value, wherein the difference between the lowest-ranked first noise level and the median value is a stability indicator value,
the one or more processors is further configured to configure the at least one filter based on the stability indicator value.

6. The system of claim 1, wherein:
each of the plurality of QRS-complex candidates is clustered into one of the at least two clusters based on the extracted one or more features of each QRS-complex candidate, wherein the at least two clusters include a first cluster corresponding to P-waves and a second cluster corresponding to R-waves.

7. The system of claim 1, wherein:
the plurality of QRS-complex candidates includes at least one QRS-complex candidate comprising an R-wave and at least one QRS-complex candidate comprising a P-wave.

8. The system of claim 1, wherein:
the one or more features of each QRS-complex candidate includes at least one of amplitude, width, peak fiducial time, and peak curvature.

9. The system of claim 8, wherein the one or more processors is configured to validate that the QRS-complex candidates of the second cluster are QRS-complexes that include respective R-waves and that QRS-complex candidates of the first cluster include respective P-waves and are not QRS-complexes.

10. The system of claim 8, wherein the one or more processors is configured to identify signal peaks in the first cluster as P-waves.

11. The system of claim 1, wherein:
based on an amplitude feature of each QRS-complex candidate, the plurality of QRS-complex candidates is clustered into a first cluster and a second cluster, wherein QRS-complex candidates of the second cluster have a larger mean amplitude than a mean amplitude of QRS-complex candidates of the first cluster.

12. The system of claim 11, wherein the one or more processors is configured to identify signal peaks in the second cluster as R-waves.

13. The system of claim 1, wherein the one or more processors is further configured to:
identify at least one R-wave from the clustered plurality of QRS-complex candidates.

14. The system of claim 13, wherein the one or more processors is further configured to:
determine at least one of an R-R interval, a P-R interval, and a P-P interval.

15. The system of claim 14, wherein the one or more processors is further configured to identify a type of heart block as a first-degree heart block based on one or more of the following conditions being satisfied during the predetermined time interval:
each P-wave is associated with a corresponding R-wave;
each P-P interval is substantially equal;
each R-R interval is substantially equal; and
each P-R interval is within a pre-determined threshold range.

16. The system of claim 14, wherein the one or more processors is further configured to identify a type of heart block as a second-degree heart block based on one or more of the following conditions being satisfied during the predetermined time interval:
R-R intervals are decreasing; and
when a heartbeat is missed, a first R-R interval including the missed heartbeat is less than or equal to twice of a second R-R interval between two consecutive heart beats.

17. The system of claim 16, wherein the type of heart block is Type I, second-degree heart block when the first R-R interval including the missed heartbeat is less than twice of the second R-R interval between two consecutive heart beats.

18. The system of claim 16, wherein the type of heart block is Type II, second-degree heart block when the first R-R interval including the missed heartbeat is equal to twice of the second R-R interval between two consecutive heart beats.

19. The system of claim 14, wherein the one or more processors is further configured to:
identify a type of heart block as a high-grade heart block when a number of R-R intervals is more than a number of P-P intervals during the pre-determined time interval.

20. The system of claim 14, wherein the one or more processors is further configured
to detect a heart block event based on the identified one or more P-waves and identify a type of heart block as a first-degree heart block based on one or more of the following conditions being satisfied during a pre-determined time interval:

each P-wave is associated with a corresponding R-wave;
each P-P interval is substantially equal;
each R-R interval is substantially equal; and
each P-R interval is within a pre-determined threshold range;
wherein the one or more processors is further configured to identify the type of heart block as a second-degree heart block based on one or more of the following conditions being satisfied during the pre-determined time interval:
R-R intervals are decreasing; and
when a heartbeat is missed, a first R-R interval including the missed heartbeat is less than or equal to twice of a second R-R interval between two consecutive heart beats.

21. The system of claim 13, wherein the one or more processors is further configured to:
identify a type of heart block as a third-degree heart block when a heart rate of the patient is lower than a pre-determined threshold during a pre-determined time interval.

22. The system of claim 1, wherein the one or more processors is configured to detect a heart block event based on the identified one or more P-waves.

23. The system of claim 1, wherein the one or more processors is configured to detect a P-wave asystole event based on the identified one or more P-waves.

24. The system of claim 1, wherein the one or more processors are further configured to generate the heart-related alarm on at least one of a physiological patient monitor, a remote platform, an external resource, or a hospital alarm output system.

25. A method comprising the steps of:
receiving an ECG signal from an ECG lead configured to be connected with a patient;
acquiring a plurality of samples from the ECG signal;
determining a noise level of the plurality of samples;
identifying a plurality of QRS-complex candidates from the ECG signal;
extracting one or more features from each QRS-complex candidate based on the determined noise level of the plurality of samples;
clustering the plurality of QRS-complex candidates into at least two clusters based on the one or more features extracted from each QRS-complex candidate;
identifying the one or more P-waves from the clustered plurality of QRS-complex candidates in real-time; and
generating a heart-rate related alarm based on the identified one or more P-waves.

26. A system comprising:
one or more processors configured to:
receive an ECG signal from an ECG lead configured to be connected with a patient;
acquire a plurality of samples from the ECG signal;
determine a noise level of the plurality of samples;
identify a plurality of QRS-complex candidates from the ECG signal;
extract one or more features from each QRS-complex candidate based on the determined noise level of the plurality of samples;
identify one or more P-waves based on the one or more features extracted from each QRS-complex candidate;
detect the P-wave asystole event based on the identified one or more P-waves; and
generate a heart-rate related alarm based on the detected P-wave asystole event.

* * * * *